(12) United States Patent
Klintenstedt et al.

(10) Patent No.: US 10,857,285 B2
(45) Date of Patent: Dec. 8, 2020

(54) SUPPORT STRUCTURE

(71) Applicant: SHL MEDICAL AG, Zug (CH)

(72) Inventors: Per Klintenstedt, Nacka (SE); Anders Boström, Solna (SE)

(73) Assignee: SHL MEDICAL AG, Zug (CH)

( * ) Notice: Subject to any disclaimer, the term of this patent is extended or adjusted under 35 U.S.C. 154(b) by 94 days.

(21) Appl. No.: 16/221,357

(22) Filed: Dec. 14, 2018

(65) Prior Publication Data

US 2019/0201612 A1 Jul. 4, 2019

(30) Foreign Application Priority Data

Jan. 4, 2018 (EP) ..................... 18150301

(51) Int. Cl.
| | |
|---|---|
| *A61M 5/24* | (2006.01) |
| *A61M 5/00* | (2006.01) |
| *A61M 5/31* | (2006.01) |
| *A61M 5/20* | (2006.01) |
| *A61M 5/32* | (2006.01) |
| *A61M 5/315* | (2006.01) |

(52) U.S. Cl.
CPC .............. *A61M 5/002* (2013.01); *A61M 5/24* (2013.01); *A61M 5/3135* (2013.01); *A61M 5/2033* (2013.01); *A61M 5/3158* (2013.01); *A61M 2005/2013* (2013.01); *A61M 2005/2418* (2013.01); *A61M 2005/2437* (2013.01); *A61M 2005/3267* (2013.01); *A61M 2209/08* (2013.01)

(58) Field of Classification Search
CPC .. A61M 2005/2418; A61M 2005/2437; A61M 2209/08; A61M 5/3135
See application file for complete search history.

(56) References Cited

U.S. PATENT DOCUMENTS

| | | | | |
|---|---|---|---|---|
| 8,821,451 B2 * | 9/2014 | Daniel | ................ | A61M 5/2033 604/187 |
| 2002/0188251 A1 | 12/2002 | Staylor et al. | | |
| 2016/0287790 A1 * | 10/2016 | Willoughby | ........ | A61M 5/2046 |

FOREIGN PATENT DOCUMENTS

| | | |
|---|---|---|
| EP | 0160711 A1 | 11/1985 |
| JP | 2004-313369 A | 11/2004 |
| WO | 2011/123024 A1 | 10/2011 |

* cited by examiner

*Primary Examiner* — Deanna K Hall
(74) *Attorney, Agent, or Firm* — McDonnell Boehnen Hulbert & Berghoff LLP

(57) ABSTRACT

The present application relates to an intermediate structure for a support structure of a medicament delivery device, which support structure is to cooperate with a medicament container, said support structure comprising a flexible element arranged to exert a force on a distal end surface of said medicament container, wherein said intermediate structure is arranged between said flexible element and said end surface and arranged to guide said flexible element in an outwardly direction in relation to a longitudinal axis (L) when exerting a force on said medicament container.

20 Claims, 6 Drawing Sheets

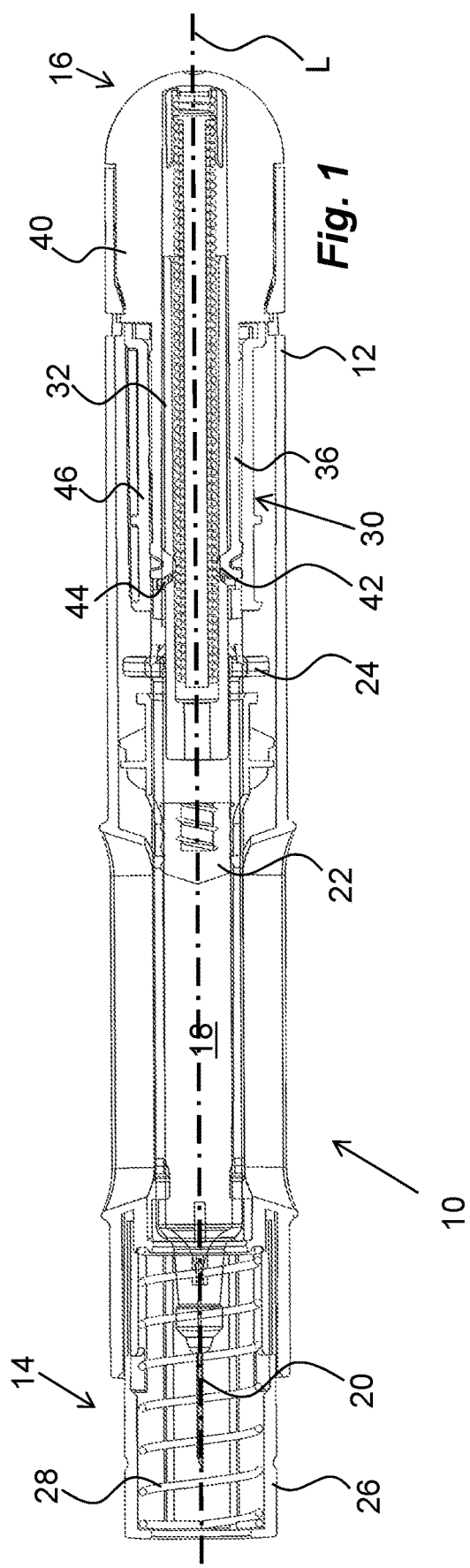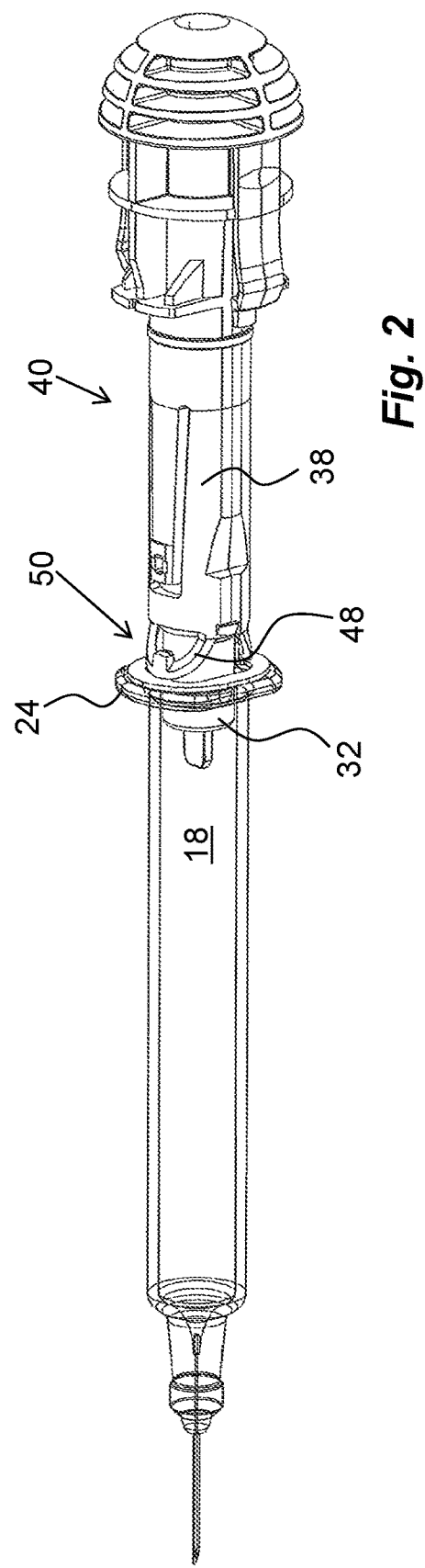

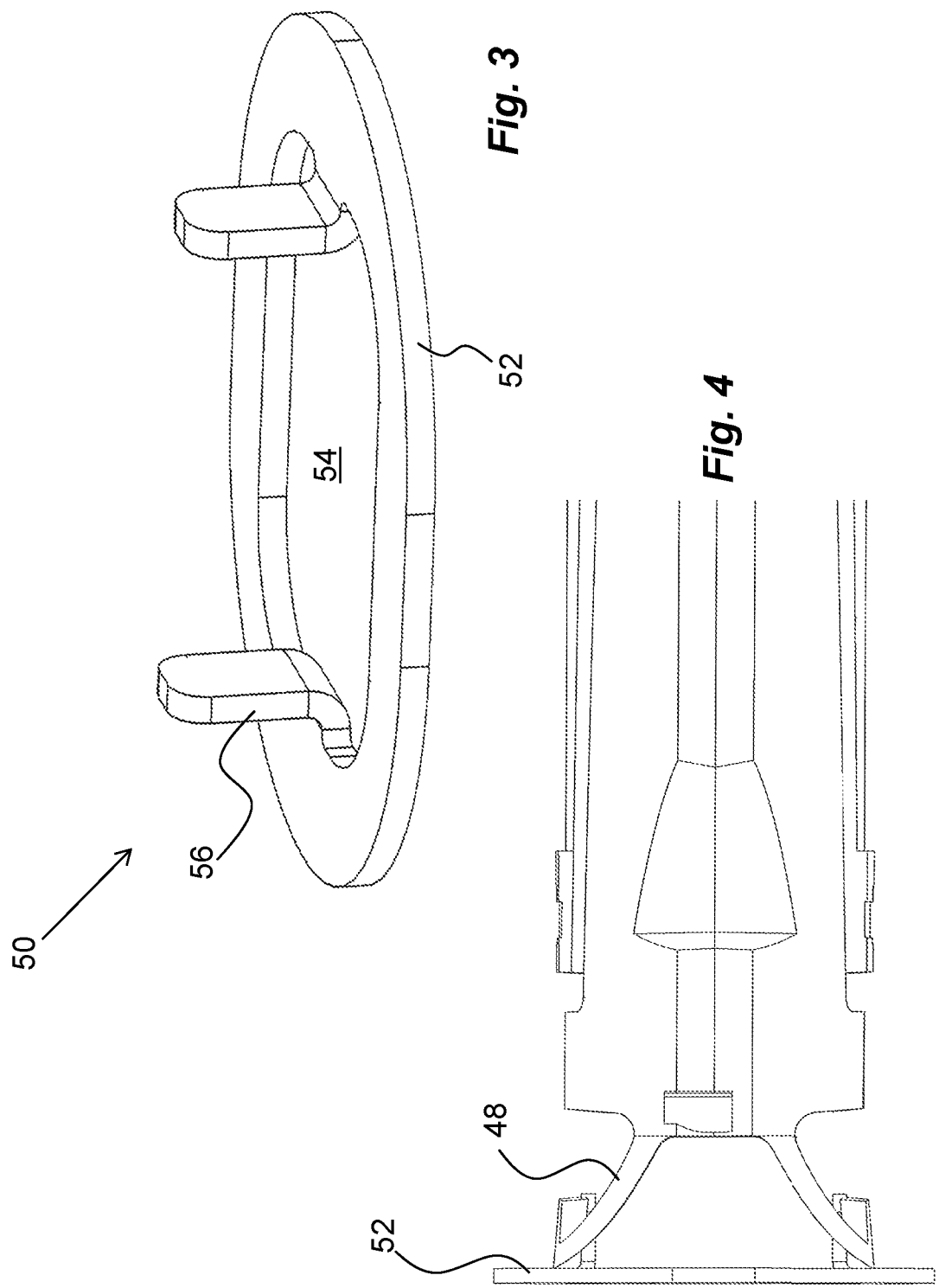

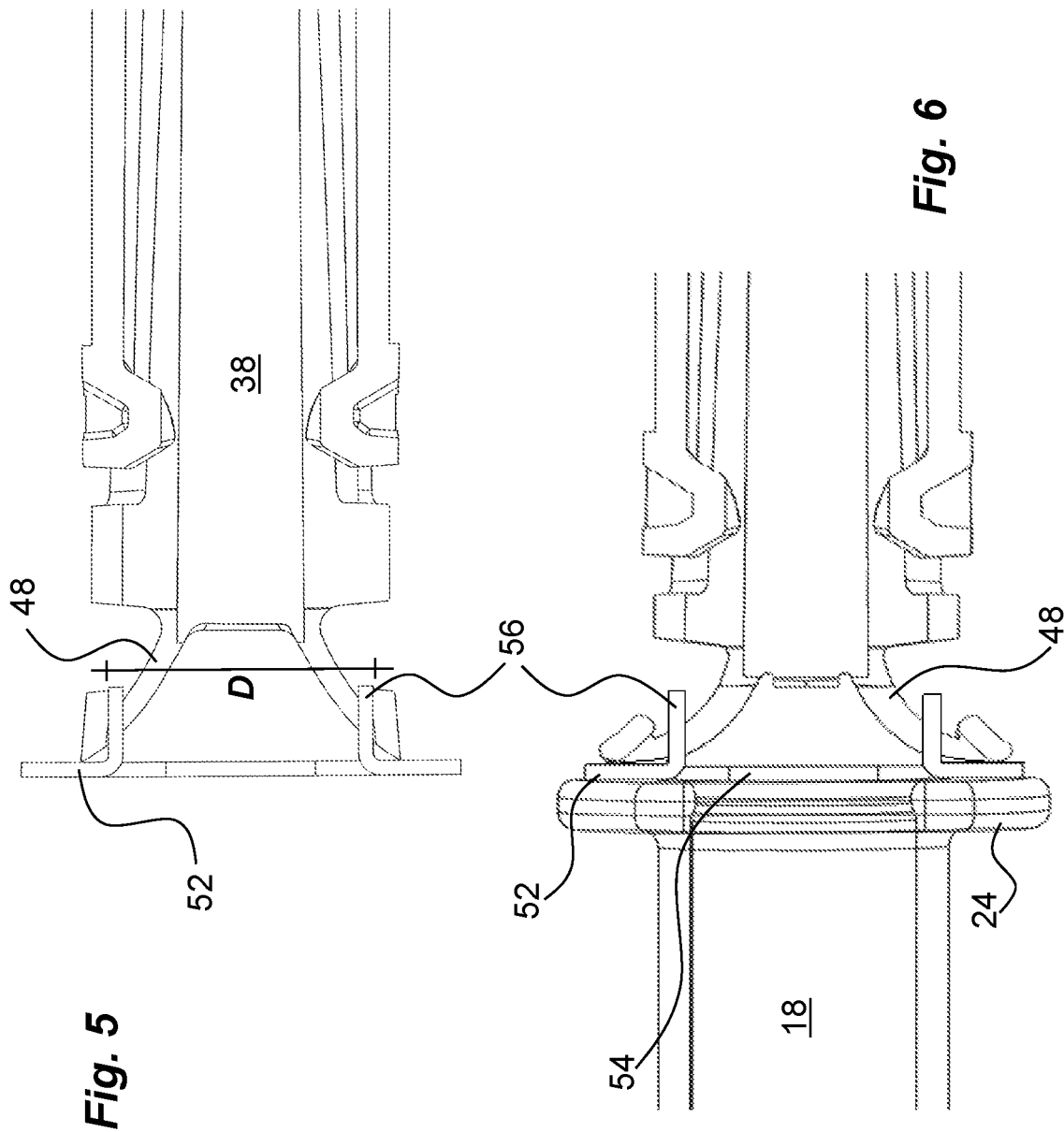

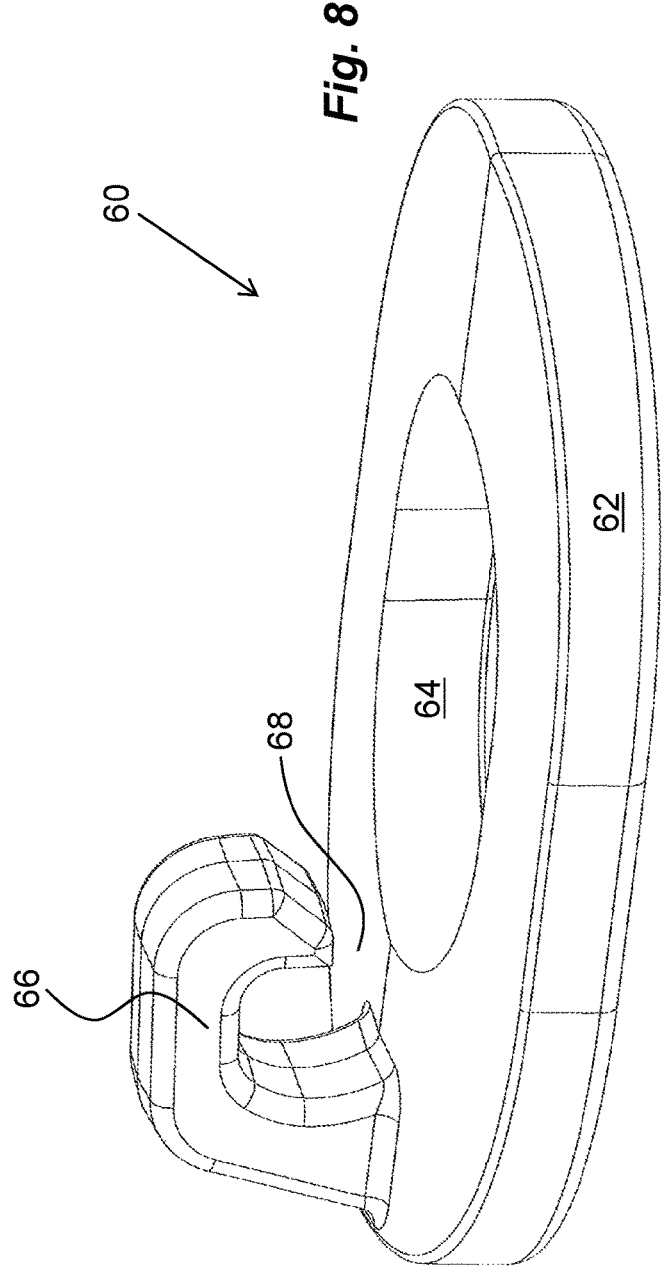
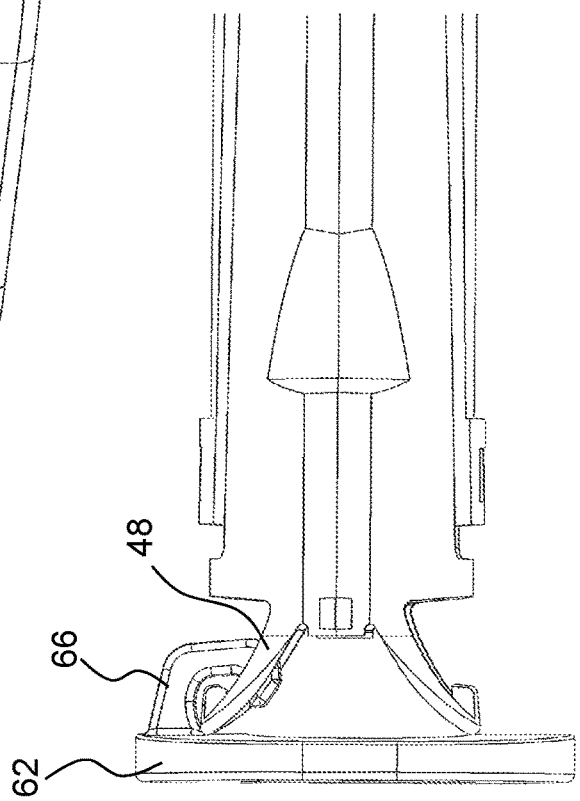

SUPPORT STRUCTURE

CROSS REFERENCE TO RELATED APPLICATIONS

The present application claims priority to European Patent Application No. 18150301.2 filed Jan. 4, 2018 which is incorporated by reference into the present application.

TECHNICAL AREA

The present application relates to a support structure for a medicament container for the purpose of holding the medicament container in a steady state inside a medicament delivery device.

BACKGROUND

Regarding medicament delivery devices having a medicament container assembled therein, it is often a desire that the medicament container is supported such that it may not rattle or move inside the housing of the medicament delivery device. Due to tolerance variations of both the medicament container and the medicament delivery device as such, any support for a medicament container should preferably be flexible and possibly also resilient in order to handle forces exerted on the medicament delivery device and thus the medicament container if it e.g. is dropped onto a hard surface.

The document WO 2011/123024 discloses a medicament delivery device provided with a number of automatic functions, which medicament delivery device has been very well received on the market. The medicament delivery device comprises a support structure in the form of arc-shaped flexible elements that are to come in contact with a distal end surface of a medicament container placed in the medicament delivery device. The support structure then exerts a force in the proximal direction of the medicament container for preventing movement of the medicament container.

In most instances this solution works very well. However, there have been instances where the medicament container delivered have had dimensions outside the specification that the medicament delivery device was designed for, and most notably there has been variations in the radius measures of the transition surface between the inner surface of the barrel of the medicament container and the distally directed surface of the flange at the distal end of the medicament container. For batches of medicament containers having large radiuses, there is a risk that the arc-shaped support structures enter into the passage of the medicament container between its inner surface and the plunger rod, thereby risking a jamming of the plunger rod and thereby a malfunction of the medicament delivery device.

SUMMARY

In the present application, when the term "distal part/end" is used, this refers to the part/end of the device, or the parts/ends of the members thereof, which during use of the device is located the furthest away from the medicament delivery site of the patient. Correspondingly, when the term "proximal part/end" is used, this refers to the part/end of the device, or the parts/ends of the members thereof, which during use of the device is located closest to the medicament delivery site of the patient.

The aim of the present application is to remedy the risks associated with the state of the art technology. The aim is solved by the features of the independent patent claims. Preferable embodiments form the subject of the dependent patent claims.

According to a main aspect of the application it comprises an intermediate structure for a support structure of a medicament delivery device, where the support structure is arranged to cooperate with a medicament container. The support structure comprises a flexible element arranged to exert a force on a distal end surface of the medicament container. The intermediate structure is arranged between the flexible element and the end surface and is arranged to guide the flexible element in an outwardly direction in relation to a longitudinal axis when exerting a force on the medicament container.

The intermediate structure thus ensures that the flexible element of the support structure is guided away from the passage of the medicament container, thus preventing or minimising the risk of a jamming of the flexible element between the medicament container and a plunger rod that is forced to push on a stopper of the medicament container for expelling a dose of medicament.

According to one feasible solution, the intermediate structure may comprise a ring-shaped element arranged to be placed at a distal passage of the medicament container. The ring-shape will have the advantages that it will not add very much to the length of the medicament delivery device since its thickness is reduced. The ring-shape will also allow the plunger rod to access the distal end of the medicament container for expelling a dose of medicament.

The intermediate structure may further comprise a guide element arranged to releasably connect to and guide the flexible element. The guide element further provides a safety against the flexible element entering into the distal end of the medicament container.

According to one aspect, the flexible element may comprise at least one arc-shaped structure arranged to a proximal end of a body of the support structure. The arc-shaped structure may extend in an inclined direction in relation to the extension of the body. Further, the guide element may comprise at least one connection element arranged to engage an outer surface of the arc-shaped structure.

According to one solution the connection element may comprise a hook, facilitating the connection of the intermediate structure with the flexible elements.

As an alternative, the connection element may comprise distally extending protrusions that are in frictional engagement with the outer surface of the arc-shaped structure. This also facilitates the connection of the intermediate structure with the flexible elements.

With this solution, when two arc-shaped structures are arranged, then two connection elements are arranged, each on an outer side surface of respective arc-shaped structure. In this regard, the connection elements may be resiliently flexible in directions transversal to the longitudinal direction.

These and other aspects of, and advantages with, the present disclosure will become apparent from the following detailed description of the disclosure and from the accompanying drawings.

BRIEF DESCRIPTION OF THE FIGURES

In the following detailed description of the present disclosure, reference will be made to the accompanying drawings, of which FIG. 1 is a cross-sectional view of a medicament delivery device that may utilize the solution according to the present application, FIG. 2 is a perspective side view of a first embodiment of an intermediate structure positioned between elements of the medicament delivery device of FIG. 1, FIG. 3 is a perspective view of the intermediate structure of FIG. 2, FIG. 4 is a side view in detail of the intermediate structure of FIG. 2 connected to a flexible element, FIG. 5 is a cross-sectional side view of the function of the intermediate structure of FIG. 2, FIG. 6 is a cross-sectional side view of the function of the intermediate structure of FIG. 2, FIG. 8 is a perspective view of the intermediate structure of FIG. 7, FIG. 9 is a side view in detail of the intermediate structure of FIG. 7 connected to two flexible elements.

DETAILED DESCRIPTION

Figure 7:
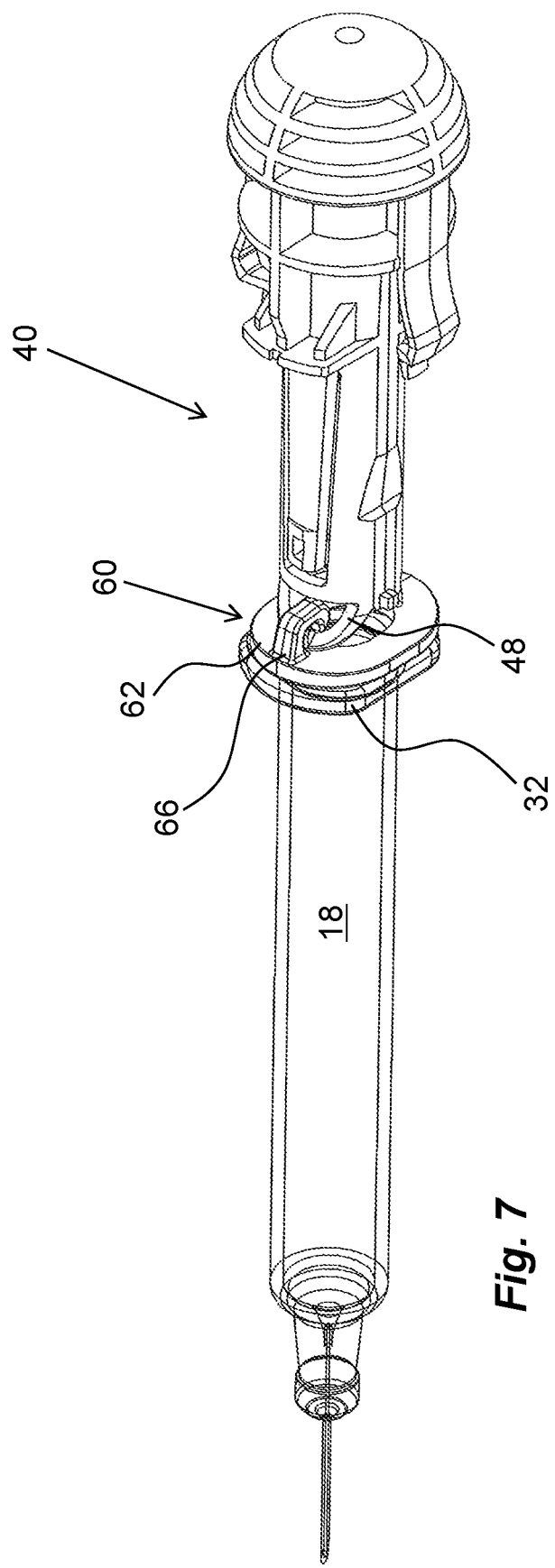
FIG. 7 is a perspective side view of a second embodiment of an intermediate structure positioned between elements of the medicament delivery device of FIG. 1.
Figure 10:
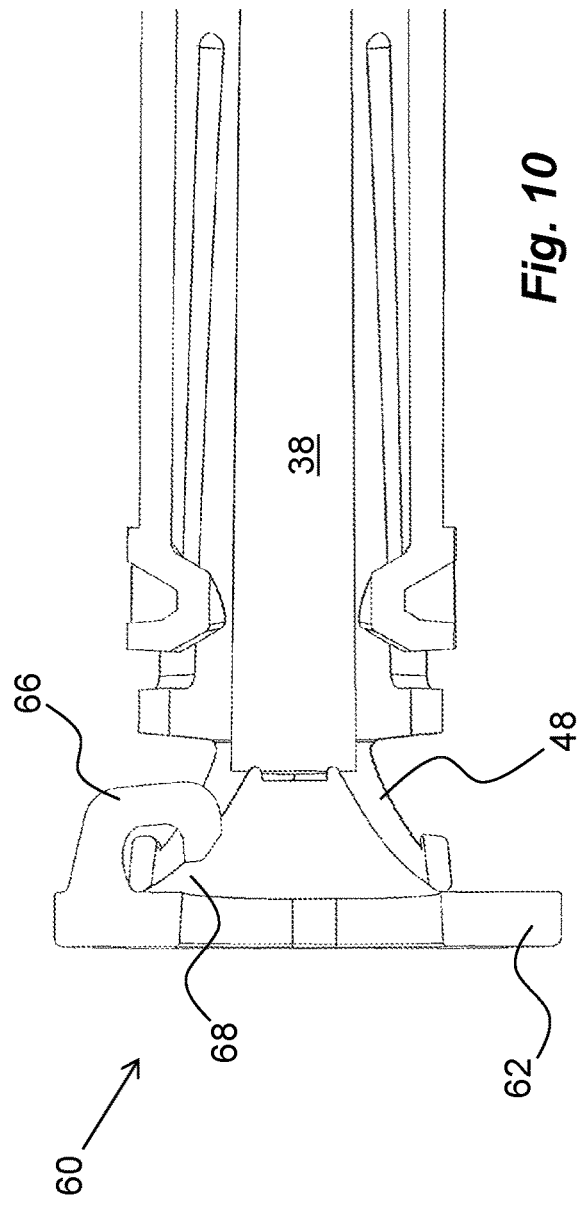
FIG. 10 is a cross-sectional side view of the function of the intermediate structure of FIG. 7.

FIG. 1 shows an example of a medicament delivery device in which the intermediate structure according to the present application may be utilized. The medicament delivery device 10 comprises an elongated housing 12 having a proximal end 14 and a distal end 16 and extending along a longitudinal axis L. The interior of the housing is arranged to accommodate a medicament container 18. The medicament container 18 shown is provided with an integrated needle 20 and has a movable stopper 22 inside the tubular body thereof. The distal end of the medicament container 18 is arranged with a radially extending flange 24. The proximal end of the housing 12 is further arranged with a generally tubular medicament delivery member guard 26 that is movable between and extended position, as shown, covering the needle 20 and a retracted position wherein a penetration may be performed with the needle 20. The medicament delivery member guard 26 is preferably urged in the proximal direction by a medicament delivery member guard spring 28. The distal end of the housing 12 is provided with a power pack 30 comprising an elongated plunger rod 32 that is arranged to act on the stopper 22 for delivering a dose of medicament through the needle 20. The plunger rod 32 is driven by a compression spring 34.

The plunger rod 32 is held with the spring 34 in a tensioned state by radially flexible arms 36 on a generally tubular body 38 of a rear cap 40, which forms a support structure. The arms 36 are provided with inwardly directed protrusions 42 that fit into recesses 44 of the plunger rod 32. The arms 36 are prevented from releasing the plunger rod 32 by a generally tubular rotator 46 positioned radially outside the arms 36 with inner surfaces of the rotator 46 in contact with outer surfaces of the arms 36. The rear cap 40 is attached to the distal end of the housing 12, wherein the distal end of the spring 34 is abutting the rear cap 40.

In order to activate the medicament delivery device, the medicament delivery member guard 26 is pushed in the distal direction. The distal part of the medicament delivery member guard 26 is arranged with elements that are capable of turning the rotator 46 such that it is no longer in contact with the arms 36. Thus the arms 36 are free to move radially outwards and thereby release the plunger rod 32 for a dose delivery sequence.

The rear cap 40 is further arranged with elements 48 that are flexible in a generally longitudinal direction and that are designed to exert a force on a distal end of the medicament container 18 when the medicament container 18 is inserted into the medicament delivery device. In the embodiment shown, the flexible elements 48 comprise two generally arc-shaped structures that are somewhat outwardly inclined in relation to the longitudinal axis of the medicament delivery device.

According to the application, an intermediate structure is arranged between the flexible elements 48 and the distal end of the medicament container 18 in order to ensure that the flexible elements 48 cannot enter into the body of the medicament container 18 and possibly get stuck or jammed between the interior of the medicament container 18 and the plunger rod 32. FIGS. 2-6 show a first embodiment of an intermediate structure 50 comprising a ring-shaped element 52 that is intended to abut the distal end surface of the flange 24 of the medicament container 18. The ring-shaped element 52 is arranged with a central passage 54 with a diameter somewhat larger than the inner diameter of the medicament container 18. The guide elements of the second embodiment comprise two distally directed protrusions or tongues 56. In the embodiment shown the tongues 56 are made integral with the ring-shaped element 52 and are created in a material that permit bending of the tongues pointing in the distal direction. It is however possible that the connection elements are made as rigid protrusions directed in the distal direction. The distance D between outer surfaces of the two tongues 56 is chosen such that when the intermediate structure 50 is connected to the flexible elements 48, the flexible elements 48 will flex radially outwards somewhat due to that the outer surfaces of the tongues 56 are in contact with the inwardly directed surfaces of the flexible elements 48, whereby a frictional connection force is obtained, FIGS. 4 and 5. The intermediate structure 50 is thus releasably connected to the flexible elements 48.

Figure 11:
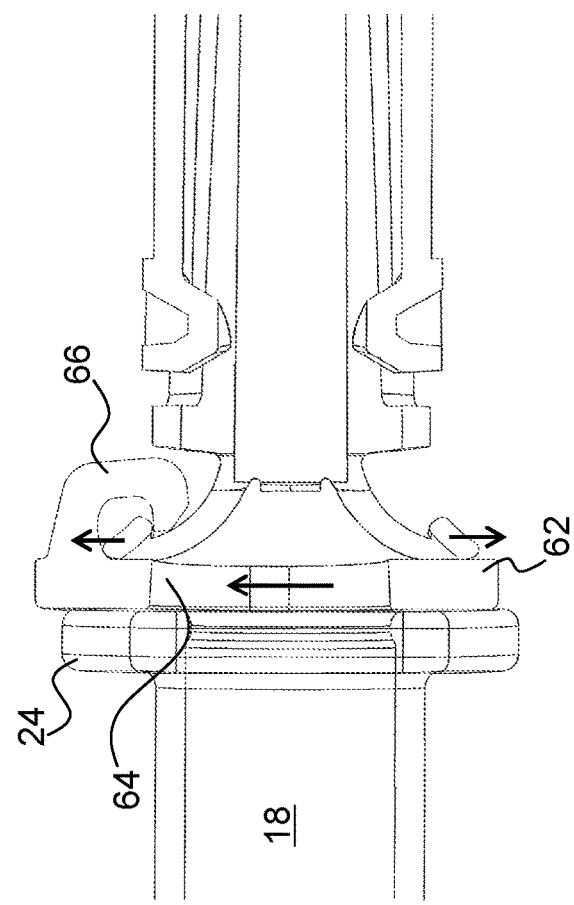
FIG. 11 is a cross-sectional side view of the function of the intermediate structure of FIG. 7.

When now the rear cap 40 is to be assembled with the medicament container 18 inside the housing, the ring-shaped element 52 of the intermediate structure 50 will abut the distal surface of the medicament container 18 whereby the flexible elements 48 will flex radially outwards, FIG. 11. Due to the connection elements 56, the flexible elements 48 are prevented from entering the distal passage of the medicament container 18. Instead, the connection elements 56 ensure that the flexible elements 48 always are flexing outwards. The flexible elements 48 will lose contact with the connection elements 56 as seen in FIG. 6, but the intermediate structure 50 will be held in place by the resilient force from the flexible elements 48, pressing the ring-shaped element 52 against the medicament container 18. The central passage 54 of the ring-shaped element 52 will then allow the plunger rod 32 to pass through during a dose delivery sequence of the medicament delivery device.

In FIGS. 7-11 a second embodiment of an intermediate structure 60 is shown. It also comprises a ring-shaped element 62 that is intended to abut a distal end surface of the medicament container 18 and in the embodiment shown a surface of the flange 24 of the medicament container 18. The ring-shaped element 62 has a central, generally circular, passage 64 that has a diameter that preferably is larger than the inner diameter of the medicament container 18, as will be explained below. One side surface of the ring-shaped element 62 is provided with a guide element 66 that in the embodiment shown is in the form of a hook having a gap 68 between the end of the hook 66 and the ring-shaped element 62, forming a connection element. In the embodiment shown the gap 68 is directed inwards. However, it is to be understood that the gap may also be directed outwards. The dimensions of the hook 66 and the measure of the gap 68 are chosen such that one of the flexible elements 48 may pass the gap 68 and be placed inside the hook 66. In this regard the cross-sectional shape of the flexible element 48 may be such that the flexible element passes the gap when the intermediate structure 60 is held in one direction and then be turned wherein the flexible element 48 cannot easily pass the gap 68, FIG. 10. As an alternative or as an addition the material of the hook 66 may be such that the hook can flex, temporarily widening the gap 68 when the flexible element 48 is pushed through the gap 68.

When the intermediate structure 60 is connected to one of the flexible elements 48$^I$ and the ring-shaped element 62 is in contact with the medicament container 18, the other flexible element 48$^{II}$ rests against the ring-shaped element 62 on the opposite side of the hook 66, FIG. 5. When now the medicament delivery device is assembled the flexible elements 48 are pressed against the ring-shaped element 62 such that they are flexing radially outwards, FIG. 6. Since one of the flexible elements 48$^I$ is connected to the hook 66, it is prevented from entering the interior of the medicament container 18. Further because of the connection, the ring-shaped element 62 will move in a radial direction as the connected flexible element 48$^I$ is flexing outwards. The movement of the ring-shaped element 62 will also reduce the risk of the second flexible element 48$^{II}$ from entering the passage of the medicament container as seen in FIG. 11.

The intermediate structure of both embodiments may be made in different materials such as metal or plastic, preferably displaying certain resilient properties. The first embodiment is preferably made of metal, providing a very thin ring-shaped element with integrated tongues, whereby the distance between the distal end of the medicament container 18 and the proximal end of the body 38 is not limited too much, providing accurate flexing action of the flexible elements 48.

It is to be understood that the embodiments described above and shown in the drawings are only to be regarded as non-limiting examples and that the present application may be modified in many ways within the scope of the patent claims.

The invention claimed is:

1. An intermediate structure for a support structure of a medicament delivery device, the intermediate structure comprising a passage and a guide element located adjacent the passage,
wherein the support structure cooperates with a medicament container and comprises an arc-shaped flexible element arranged to exert a force on a distal end surface of said medicament container,
wherein said intermediate structure is arranged between and engages said flexible element and said distal end surface and is arranged to guide said flexible element in an outwardly direction in relation to a longitudinal axis (L) when exerting a force on said medicament container.

2. The intermediate structure according to claim 1, comprising a ring-shaped element arranged to be placed at a distal passage of said medicament container.

3. The intermediate structure according to claim 1, where the guide element is arranged to releasably connect to and guide said flexible element.

4. The intermediate structure according to claim 3, wherein said flexible element is arranged to a proximal end of a body of said support structure and extending in an inclined direction in relation to the extension of the body and wherein said guide element are arranged to engage an inner surface of said arc-shaped structure.

5. The intermediate structure according to claim 4, wherein said guide element comprises distally extending elements that are in frictional engagement with the inner surface of the arc-shaped structure.

6. The intermediate structure according to claim 5, wherein two arc-shaped structures are arranged and wherein two guide elements are arranged, each on an inner side surface of respective arc-shaped structure.

7. The intermediate structure according to claim 6, wherein said guide elements are resilient tongues flexible in directions transversal to a longitudinal direction (L).

8. The intermediate structure according to claim 4, wherein said guide element comprises a hook.

9. The intermediate structure according to claim 4, wherein said body is arranged to accommodate a plunger rod and wherein the passage is sized to allow axial movement of the plunger rod therethrough.

10. An assembly for cooperating with a medicament container in a medicament delivery, the assembly comprising:
an intermediate structure having a passage and a guide element located adjacent the passage; and
a support structure operatively engaged with the intermediate structure and comprising an arc-shaped flexible element arranged to exert a force on a distal end surface of the medicament container and is engaged with the guide element.

11. The assembly of claim 10, where the guide element is engaged with the flexible element to guide the flexible element in an outwardly direction in relation to a longitudinal axis (L) when the intermediate structure is exerting a force on the medicament container.

12. The assembly of claim 10, where the intermediate structure further comprises a ring-shaped element having a proximal end surface configured for positioning at a distal passage of the medicament container.

13. The assembly of claim 10 wherein the flexible element extends in an inclined proximal direction and wherein the guide element is arranged to engage an outer surface of the arc-shaped structure.

14. The assembly of claim 10 where the guide element further comprises at least two distally extending elements that are in frictional engagement with the flexible element.

15. The assembly of claim 14 wherein the flexible element comprises at least two arc-shaped structures extending in an inclined proximal direction that are arranged to engage the at least two distally extending elements.

16. The assembly of claim 14, where the at least two distally extending elements are resilient tongues flexible in directions transversal to a longitudinal direction (L).

17. The assembly of claim 14, where each of the at least two distally extending elements comprise a hook.

18. A medicament delivery device comprising:
an intermediate structure having a passage and a guide element located adjacent the passage;
a support structure comprising two arc-shaped structures operatively engaged with the intermediate structure; comprising,
wherein the support structure cooperates with a medicament container, the support structure comprising a flexible element arranged to exert a force on a distal end surface of the medicament container, wherein the intermediate structure is arranged between the flexible element and the end surface and arranged to guide the flexible element in an outwardly direction in relation to a longitudinal axis (L) when exerting a force on the medicament container.

19. The medicament delivery device of claim 18, where the intermediate structure further comprises a proximal end face that is in contact with a proximal end of the medicament container and where the guide element comprises two flexible tongues engaged with the two arc-shaped structures.

20. The medicament delivery device of claim 18, where the guide element is a hook that is engaged with the flexible element that comprises an arc-shaped structure.

* * * * *